US009456794B2

(12) United States Patent
Carpenter et al.

(10) Patent No.: US 9,456,794 B2
(45) Date of Patent: Oct. 4, 2016

(54) MOLECULAR IMAGING USING RADIOLUMINESCENT NANOPARTICLES

(75) Inventors: Colin M Carpenter, Redwood City, CA (US); Lei Xing, Palo Alto, CA (US); Guillem Pratx, Mountain View, CA (US); Conroy Ghin Chee Sun, Sunnyvale, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 929 days.

(21) Appl. No.: 13/066,190

(22) Filed: Apr. 8, 2011

(65) Prior Publication Data

US 2011/0251484 A1    Oct. 13, 2011

Related U.S. Application Data

(60) Provisional application No. 61/322,296, filed on Apr. 9, 2010.

(51) Int. Cl.
*A61B 6/00* (2006.01)
*A61B 6/03* (2006.01)

(52) U.S. Cl.
CPC ............ *A61B 6/4057* (2013.01); *A61B 6/032* (2013.01); *A61B 6/425* (2013.01); *A61B 6/508* (2013.01)

(58) Field of Classification Search
CPC .................................................. A61B 6/4057
USPC ................................................ 600/473–476
See application file for complete search history.

(56) References Cited

U.S. PATENT DOCUMENTS

| | | | | |
|---|---|---|---|---|
| 4,281,910 A | * | 8/1981 | Takayama | 396/17 |
| 7,155,274 B1 | * | 12/2006 | Wake et al. | 600/476 |
| 7,367,948 B2 | * | 5/2008 | O'Donnell et al. | 600/458 |
| 7,725,169 B2 | * | 5/2010 | Boppart et al. | 600/473 |
| 2004/0092825 A1 | * | 5/2004 | Madar et al. | 600/473 |
| 2007/0063154 A1 | | 3/2007 | Chen et al. | |
| 2007/0238957 A1 | * | 10/2007 | Yared | 600/407 |

OTHER PUBLICATIONS

Bentolila et al, "Quantum Dots for In Vivo Small-Animal Imaging," J. Nucl. Med., 2009, vol. 50, pp. 493-496.
Michalet, et al., "Quantum Dots for Live Cells, in Vivo Imaging, and Diagnostics," Science, 2005, vol. 307, pp. 538-544.
Ntziachristos, "Fluorescence Molecular Imaging," Annu. Rev. Biomed. Eng., 2006, vol. 8, pp. 1-33.
Soltesz et al., "Intraoperative Sentinel Lymph Node Mapping of the Lung Using Near-Infrared Fluorescent Quantum Dots," Ann. Thorac. Surg., 2005, vol. 79, pp. 269-277.

* cited by examiner

*Primary Examiner* — Rochelle Turchen
(74) *Attorney, Agent, or Firm* — Lumen Patent Firm (57) ABSTRACT

Molecular imaging of radioluminescent nanoparticle probes injected into biological tissue is performed by irradiated the tissue with ionizing radiation to induce radioluminescence at optical wavelengths, preferably at predetermined near infrared wavelengths. The optical light is detected and processed to determine a spatial distribution of the probes. The radioluminescent nanoparticles may be inorganic or organic phosphors, scintillators, or quantum dots. Imaging systems realizing this technique include tomographic systems using an x-ray beam to sequentially irradiate selected regions, systems with a radioactive source producing the ionizing radiation from outside the tissue, such as with a beam, or inside the tissue, such as with an endoscope or injected radiopharmaceutical. The optical signals may be detected by a photodetector array external to the tissue, a photodetector integrated with an endoscope or mammographic paddle, integrated into a capsule endoscope, or an array positioned near the biological tissue.

17 Claims, 4 Drawing Sheets

MOLECULAR IMAGING USING RADIOLUMINESCENT NANOPARTICLES

CROSS-REFERENCE TO RELATED APPLICATIONS

This application claims priority from U.S. Provisional Patent Application 61/322,296 filed Apr. 9, 2010, which is incorporated herein by reference.

STATEMENT OF GOVERNMENT SPONSORED SUPPORT

This invention was made with Government support under contract 0854492 awarded by National Science Foundation, and under contract CA 104205 awarded by National Institutes of Health (NIH). The Government has certain rights in this invention.

FIELD OF THE INVENTION

The present invention relates generally to molecular imaging methods and systems. More specifically, it relates to molecular imaging using ionizing radiation to stimulate light emission from molecular probes containing radioluminescent nanoparticles.

BACKGROUND OF THE INVENTION

Medical imaging using x-rays is sensitive to differences in the density and composition of tissues such as bone, muscle, and fat. Many diseases, however, are only poorly detected or are completely undetectable in this manner. Molecular imaging has the potential to increase disease detection sensitivity and specificity through the use of molecular probes, or biomarkers, designed to bind to specific biological targets, such as proteins in the body that signal cellular events, such as apoptosis, angiogenesis, hypoxia, and other disease markers. A few contrast agents, such as iodine or barium sulfate, can be imaged with x-rays; however, the low sensitivity of these contrast agents requires significant (often toxic) doses of contrast agents to identify injected contrasts. Thus, x-ray imaging alone is intrinsically unable to perform molecular imaging. Other types of molecular imaging use radiotracers as biomarkers, i.e., radioactive materials that bind to a specific biological targets, and special detectors to sense the ionizing radiation emitted from these radioactive biomarkers. These also involve significant radiation dose.

Current optical molecular imaging use optical excitation with optical emission. For example, there are several instruments that image molecular markers using optical fluorescence. These systems use optical light, e.g., from a laser, to excite fluorescent dyes attached to molecular targets. Optical molecular imaging has also been proposed using up-conversion phosphors. In these techniques, the phosphors are irradiated with infrared energy from a laser, causing them to produce optical light at a lower wavelength. Unfortunately, due to the absorption of the exciting infrared light by water/tissue, combined with the absorption of the emitted optical light from the phosphors, these optical molecular imaging techniques do not provide a strong signal for imaging.

SUMMARY OF THE INVENTION

The present invention provides techniques for molecular imaging using ionizing radiation to stimulate optical light emission from molecular probes containing radioluminescent nanoparticles. The approach of the present invention offers alternatives to all-optical molecular imaging methods, such as fluorescence imaging. In some embodiments, for example, radioluminescence offers better depth sensitivity, because it can use excitation signals (e.g., x-rays or gamma rays) with high penetration depth. In addition, this technique has an increased signal-to-noise ratio because radioluminescence imaging avoids tissue auto-fluorescence, a phenomenon common in fluorescence imaging. Thus, in some embodiments, simple photodetection instrumentation can be attached to clinical x-ray instruments to detect emitted light. Finally, a coupled x-ray optical system according to some embodiments provides inherent co-registration of anatomical x-ray and molecular optical images, which allows for accurate synergy of structural and functional information.

In one aspect, a method for molecular imaging is provided in which radioluminescent nanoparticle probes that have been injected into biological tissue are irradiated with ionizing radiation to induce radioluminescence at optical wavelengths. The optical light is detected and processed to determine a spatial distribution of the probes in the biological tissue.

The molecular probes injected into the biological tissue include radioluminescent nanoparticles and are designed to preferentially bind to a predetermined biological target within the biological tissue. For example, the radioluminescent nanoparticles may be inorganic or organic phosphors or scintillators. The radioluminescent emission of light from the radioluminescent nanoparticles has a wavelength in the optical spectrum, defined herein to include visible, ultraviolet, and infrared wavelengths. Preferably, the radioluminescent emission of optical light is at a predetermined near infrared (NIR) wavelength. In some embodiments, multiple types of radioluminescent nanoparticles, composed of distinct materials having distinct predetermined optical emission wavelengths, are imaged concurrently to probe multiple distinct predetermined biological targets.

The irradiation of the selected region of the biological tissue with ionizing radiation induces radioluminescence emission of optical light from molecular probes that are located in the selected region. The ionizing radiation may include alpha particles, beta particles (electrons or positrons), electron beams, proton beams, gamma rays, ultraviolet light, or x-ray radiation. In some embodiments, irradiating the selected region of the biological tissue with ionizing radiation is performed by scanning the biological tissue with a computer-controlled, collimated x-ray beam to selectively irradiate a sequence of selected regions. In another embodiment, irradiating the selected region of the biological tissue with ionizing radiation is performed by applying a broad beam of x-ray which stimulates the entire tissue volume under observation. In other embodiments, irradiating the selected region of the biological tissue with ionizing radiation is performed by positioning a radioactive material producing the ionizing radiation near the selected region. For example, a radiopharmaceutical compound that emits the ionizing radiation may be injected into the biological tissue. In another embodiment, a radioactive material producing the ionizing radiation may be attached to an endoscope positioned near the biological tissue during a medical procedure. Such an endoscope may have a retractable shield to selectively block the ionizing radiation, and collimators to selectively direct the ionizing radiation.

The optical light from the irradiated molecular probes is detected to produce signals which are then processed to determine a spatial distribution of the irradiated molecular probes in the biological tissue. For example, in some embodiments, the optical signals may be detected using one or more photodetector arrays which may be screened from x-ray interference. In other embodiments, the optical light may be detected by photodetectors within a capsule endoscope or coupled through an endoscope from a distal end to a photodetector at a proximal end.

The signals resulting from the detection of the optical signals are then processed for determining the spatial distribution of the molecular probes and/or assessing a presence and concentration of the molecular probes in the biological tissue. For example, the signals may be processed to produce an image representative of the spatial distribution of the irradiated molecular probes in the biological tissue. In embodiments where irradiating the selected region of the biological tissue with ionizing radiation is performed by scanning the selected region with a computer-controlled, collimated x-ray beam, the processing of the signals may include performing a tomographic reconstruction of the spatial distribution of the irradiated molecular probes in the biological tissue. In some embodiments, the molecular imaging and tomographic reconstruction may be performed simultaneously with x-ray imaging of the biological tissue to produce x-ray imaging data to permit co-registration of the x-ray imaging data with the spatial distribution of the irradiated molecular probes.

In another aspect, a system is provided for molecular imaging of radioluminescent nanoparticles. The system includes a source of ionizing radiation, such as a radioactive material or x-ray imaging source, a detector of optical wavelengths of light emitted from the radioluminescent nanoparticles irradiated by the ionizing radiation, and a signal processor for determining a distribution of the radioluminescent nanoparticles in a region of biological tissue irradiated by the ionizing radiation.

In one embodiment, the source is a computer-controlled, collimated x-ray beam source, the detector includes a photodetector array, and the processor performs a tomographic reconstruction of the spatial distribution of the radioluminescent nanoparticles in the biological tissue.

In another embodiment, the source is an external x-ray beam, or a radioactive material such as a radiopharmaceutical compound injected into the biological tissue, and the detector is a photodetector attached or optically coupled to the distal end of an endoscope, integrated into a capsule endoscope, or an array positioned near the biological tissue. In another embodiment, the radioactive material is attached to the distal end of an endoscope, and the detector is a photodetector optically coupled to the distal end of the endoscope. Such an endoscope may have a retractable shield to selectively block the ionizing radiation from the radioactive material, and collimators to selectively direct the ionizing radiation.

The methods and systems of the present invention have applications to biomedical imaging (e.g., for cancer, neurodegenerative diseases, heart disease) and to pre-clinical imaging (e.g., for drug development and fundamental research).

DETAILED DESCRIPTION

Figure 1:
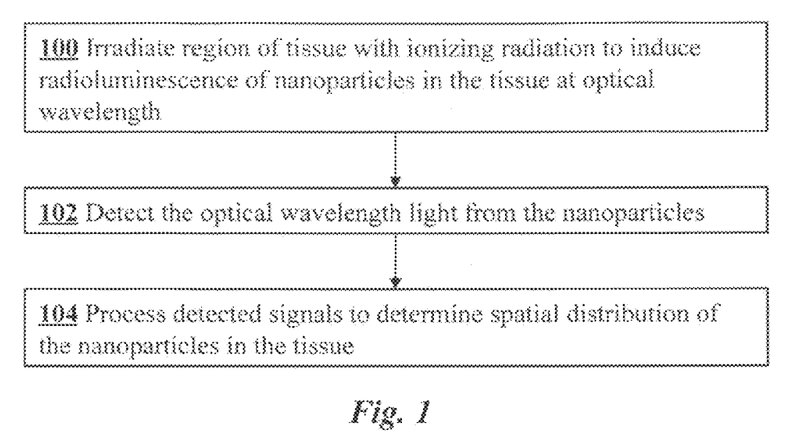
FIG. 1 is a flowchart outlining the main steps of a method for molecular imaging according to an embodiment of the invention.

FIG. 1 is a flowchart outlining the main steps of a method for molecular imaging according to an embodiment of the invention. Radioluminescent nanoparticle probes that have been injected into biological tissue preferentially bind to biological targets in a tissue. The method images these molecular probes using ionizing radiation to induce radioluminescence at optical wavelengths in step 100. The irradiation of the selected region of the biological tissue with ionizing radiation induces radioluminescence emission of optical light from molecular probes that are located in the selected region. The ionizing radiation may include ultraviolet, alpha, beta, gamma, or x-ray radiation. The optical light from the nanoparticle probes is detected in step 102 to produce representative signals, and these signals are processed in step 104 to determine a spatial distribution of the probes in the tissue.

Radioluminescent Nanoparticle Probes

The molecular probes injected into the biological tissue are designed to preferentially bind to a predetermined biological target within the biological tissue. The probes include radioluminescent nanoparticles such as inorganic or organic phosphors, scintillators, and semiconductor quantum dots, which emit optical light when irradiated by ionizing radiation. Preferably, the radioluminescent emission of light occurs at a near infrared (NIR) wavelength. In particular, the nanoparticles are more preferably fabricated to emit light during radioluminescence at a specific predetermined NIR wavelength. In some embodiments, two or more distinct molecular probes are used with distinct radioluminescent materials to allow concurrent discrimination of different biological targets. For example, a first molecular probe that preferentially binds to a first predetermined biological target has a first radioluminescent material with a first predetermined optical emission wavelength, and a second molecular probe that preferentially binds to a second predetermined biological target has a second radioluminescent material with a second predetermined optical emission wavelength, where the first and second biological targets, radioluminescent materials, and optical emission wavelengths are distinct from each other. Scintillator phosphors, for example, can be tuned to emit different wavelengths of light based on the doping material; for example, Terbium is known to emit green (545 nm) light, while Thulium is know to emit near-infrared (802 nm) light, which is ideal for low absorption in tissue. These phosphors show a surprisingly large light output in the liquid environment of biological tissue.

Various radioluminescent nanoparticles may be used in the molecular probes. One type of suitable material are nanophosphors which can be excited by high energy (i.e., greater than 1 keV) photons or electrons. For example, the probes may include ($La_2O_2S$:Tb) nanoparticles which emit a sharp peak near 550 nm under the irradiation of a 100 keV, 20 mA, x-ray beam. These particles may be fabricated to a size of less than 50 nm. In general, longer near-infrared wavelengths are preferable for imaging in deep tissue due to lower tissue absorption at longer wavelengths. Accordingly, the molecular probes may include a YAG:Tm nanoparticle, which has an emission wavelength near 800 nm. Other radioluminescent materials which may be used to form the nanoparticles include $Gd_2O_2S$:Tb, $Gd_2O_2S$:Eu, $La_2O_2S$:Tb, $La_2O_2S$:Eu, ZnS:Eu, ZnO:Eu, $BaYF_5$:Tb, $BaYF_5$:Eu and $Ba_{0.55}Y_{0.3}F_2$:Eu with dopant concentrations ranging from 0.5-15 mole %. Gadolinium oxysulfide phosphors may be prepared with standard methods and doped with Terbium to form $Gd_2O_2S$:Tb nanoparticles with a size of about 50 nm. Functionalization of the nanoparticle surface can be performed by surface modification with biocompatible polymers such as poly(ethylene glycol) (PEG) through physical adsorption, electrostatic binding, or covalent bonding. To impart biological specificity, chemical functional groups (e.g. amine, carboxyl, thiol, etc.) incorporated on the terminal ends of the polymer coating can be employed to covalently link targeting agents such as high affinity small molecules, peptides, proteins, and antibodies. Alternatively, biological binding through biotin-streptavidin complexes can be employed for bioconjugation of cell specific ligands.

Methods for molecular imaging according to the invention may be understood and illustrated by reference to various types of molecular imaging systems. A system for molecular imaging of radioluminescent nanoparticles includes a source of ionizing radiation, such as a radioactive material or x-ray imaging source, a detector of optical wavelengths of light emitted from the radioluminescent nanoparticles irradiated by the ionizing radiation, and a signal processor for determining a distribution of the radioluminescent nanoparticles in a region of biological tissue irradiated by the ionizing radiation.

Tomography System Using X-Ray Source

Figure 2:
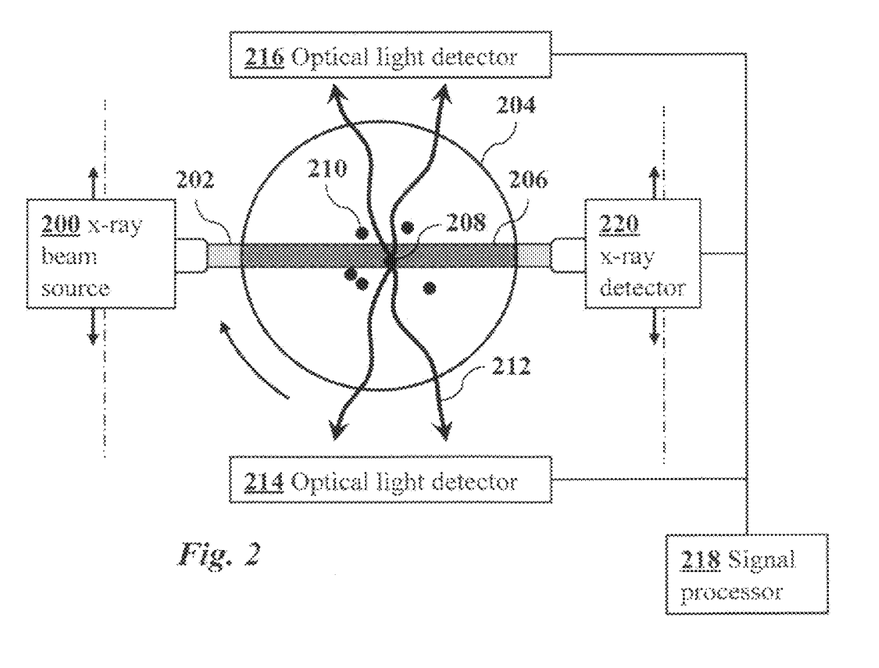
FIG. 2 is a schematic diagram of a system for molecular imaging using an x-ray beam source, according to an embodiment of the invention.

FIG. 2 is a schematic diagram of a system for molecular imaging according to an embodiment of the invention. In this embodiment, the source of ionizing radiation is a computer-controlled, collimated x-ray beam source 200 which emits a collimated x-ray beam 202 directed at the biological tissue 204. The beam 202 intersects the tissue 204 in a region 206 that is selected by computer-controlled translational and/or rotational positioning of the source 200 relative to the tissue 204, as is well-known in the art of tomographic imaging.

The tissue 204 contains a distribution of radioluminescent nanoparticle probes such as probes 208 and 210. The x-ray beam 202 selectively irradiates the probes within the selected region 206, without irradiating other probes in the tissue. For example, probe 208 is irradiated in the specific configuration shown in FIG. 2, while probe 210 is not. Consequently, probe 208 emits radioluminescent light at optical wavelengths 212 which is detected by an optical light detector array 214, e.g., a near-infrared (NIR) detector, preferably oriented parallel to the beam 202. Array 214 may be a charge coupled device (CCD) array, photodiode array, photomultiplier tube, or avalanche photodiode array. In some embodiments, one or more additional arrays, such as array 216 may also be included to detect the radioluminescent light from the probes. The photodetector arrays 214 and 216 are preferably screened from x-ray interference, e.g., with transparent lead glass and lead walls having thicknesses of at least 6 mm.

During a scanning procedure, the x-ray beam source 200 is translated and/or rotated relative to the tissue 204 by a computer controller (not shown) to select different regions of the biological tissue for irradiation. This relative translation and/or rotation may involve, for example, translational movement of the beam source 200 combined with rotation of the tissue 204, or both translation and rotation of the beam source (in which case the optical detector 214 is also rotated). In some embodiments, optical light detector 214 is an array that collects light from any irradiated region of the tissue. A fixed zoom camera lens may be used to allow a large enough field of view to capture images of the selected regions of the tissue. In other embodiments, light detector 214 may include a lens to provide a narrow field of view and translational mechanism to allow scanning of selected detection regions within the selected irradiation region. A processor 218 receives signals from the detector 214 (and from other detectors such as 216 if present) at the various selected translational and/or rotational positions. Optical signals diffusing out of the tissue can be interpreted as projective measurements. Combining these signals with a priori position knowledge from the computer controller, the processor 218 produces a tomographic reconstruction of the spatial distribution of the radioluminescent nanoparticle probes in the biological tissue. Maximum likelihood expectation maximization (ML-EM) is one possible reconstruction algorithm.

In some embodiments, the position and angle of the beam is moved around the subject during the scan. In other embodiments, additionally, the shape and intensity of the beam can be modulated. For example, the scanning may include a quick, low resolution scan with a broad beam, followed by a more narrow beam focused in an area of interest to obtain higher spatial resolution in that area.

In some embodiments, the molecular imaging and tomographic reconstruction described above may be performed simultaneously with x-ray tomographic imaging of the biological tissue. For example, an x-ray detector 220 may be included in the system and positioned opposite the x-ray beam source 200. Detector 220 and beam source 200 translate and/or rotate together relative to the tissue 204. Detector 220 collects x-ray imaging data at each translational and/or rotational position of a scan. This data may then be combined with the imaging data from the optical light detectors 214 and 216 to permit co-registration of the x-ray imaging data with the spatial distribution of the irradiated molecular probes. The conventional x-ray equipment combined with the molecular imaging could be any imaging instrument which uses an x-ray source, including mammography, computed tomography (CT), fluoroscopy, projection x-ray, brachytherapy and radiotherapy beams.

A limitation of existing optical imaging systems is that they have a resolution limit due to the high light scattering which effects measurements in deep tissue. However, by exciting a narrow volume of tissue with a high resolution x-ray beam, high-resolution optical images can be produced since the localization of the molecular probes is inferred from the x-ray excitation. In addition, structural anatomical features can be used to improve the image resolution of optical imaging. Embodiments of the present invention allow perfect image co-registration because the x-ray system is used to activate the optical system during simultaneous operation. Thus, by synchronizing the x-ray system operation with the optical detection hardware, true image co-registration can be performed.

In principle, it is possible to apply bioluminescence tomography (BLT) techniques to reconstruct the 3-D distribution of these light sources. Yet, the number of photons produced for standard radiation dose limits the accuracy of the images that can be reconstructed from such diffuse measurements. Instead, a selective excitation scheme may be used for obtaining high-quality images from a limited number of photons. In this scheme, herein called x-ray luminescence computed tomography (XLCT), selected regions of the tissue are irradiated by a sequence of narrow x-ray beams positioned at predefined locations, while photodetectors measure the radioluminescent light emitted from the nanoparticles in the tissue. Regardless of where photons are detected, it is known that those photons originated somewhere within the selected region irradiated by the x-ray beam. Hence, through this selective excitation mechanism, XLCT produces projective measurements similar to those recorded in conventional CT.

A computer-controlled motion stage may be used to rotate and/or translate the tissue with respect to the x-ray beam and generate a projection signal. The x-ray source may be operated with voltage and current set to 50 kV and 30 mA, respectively, and the beam filtered with 0.4 mm Al. In one illustrative scan, the tissue may be translated 20 times in increments of 3 mm, and rotated 16 times to cover 360 degrees, both relative to the source and detector. Lead may be used to create a 5 mm-wide slit and collimate the x-ray beam. More preferably, a tungsten collimator may be used to improve spatial resolution and reduce x-ray scatter.

For each beam position, the images may be acquired with an electron-multiplying charge-coupled device (EM-CCD) camera (ImagEM C9100-13, Hamamatsu), using 512×512 pixels, an exposure time of 1 s and an EM gain of 160. Although the CCD is preferably partially shielded with lead, scattered x-rays may nevertheless create hot spots in the images which may be removed by special image processing. In one embodiment, the signal may be formed by summing the value of all the pixels together after correcting for dark noise. By running the CCD camera as a "single-pixel detector", the image formation mechanism of XLCT is based on a simple selective excitation scheme rather than complex optical measurements and reconstruction.

During processing, the CCD measurements may be binned into a sinogram and reconstructed with 20 iterations of an iterative expectation-maximization maximum-likelihood (ML-EM) algorithm which models the physical response of the imaging system.

The linear response of the reconstructed signal relative to the input nanophosphor concentration indicates that XLCT is a quantitative imaging modality. The x-ray scatter background is the cause of the constant offset in the response linearity curve for the experimental dataset.

In another illustrative scan, the tissue may be translated 26 times in increments of 1 mm, and rotated 24 times, covering 360 degrees. The x-ray beam may be collimated by two lead bricks separated by a 1 mm gap. A f/1.4 lens connected to the CCD camera serves as the optical detection system. The distribution of the light escaping the tissue is recorded for each beam position. During processing, a region-of-interest (ROI) may be automatically drawn around the position of the tissue in each CCD frame, and the signal from all the pixels within the ROI summed to produce a 24×26 sinogram, which is reconstructed with 100 iterations of ML-EM. The x-ray selective excitation encodes the position of the emitted photons with sufficient accuracy to reconstruct tomographic images with high fidelity, despite optical scatter.

Although spatially-resolving optical detectors are not required for imaging, measuring the spatial distribution of the light diffusing out of the tissue provides additional information to improve image quality. For instance, hybrid reconstruction may be performed by combining a model of the tissue ionization by the x-ray beam and an optical model of the light diffusion through tissue. In such hybrid approach, the selective excitation constrains the optical source to either a 1-D line or a 2-D plane. As a result, solving for the light source distribution based on the optical measurements is a better-posed inverse problem.

The following image reconstruction model has been developed to obtain distributions of the radioluminescent nanoparticles in vivo. This reconstruction model incorporates a diffuse optical imaging light propagation approach to model emitted light propagation. The optical light propagation is based on the diffusion approximation of optical light in tissue:

$$-\nabla \cdot D \nabla \Phi_M(r, t) + \mu_a \Phi_M(r, t) = \frac{\eta c}{E_{ph}} \int De^{\frac{-(t-t')}{\tau}} dt$$

The luminescence output fluence, $\Phi_M$, in units of ph/s/mm$^3$, from the nanophosphors is affected in the tissue by absorption and scatter, characterized by the coefficients, $\mu_a$ and D, respectively, where $$D = \frac{1}{3(\mu_a + \mu_s')}$$

The light yield is due to the phosphor quantum yield, $\eta$, the concentration of the phosphors, c (in units of mm$^3$ phosphor/mm$^3$ tissue), D is the dose rate of the irradiation, in units of J/s/mm$^3$, and the phosphor decay time is denoted by $\tau$.

The phosphor quantum yield and decay times have been computed for many different phosphors in the literature. The electron fluence density can be calculated from Monte Carlo software which is freely available (e.g., GEANT 4 (CERN), and EGSnrc (LBNL)).

Radioluminescent Imaging with a Radioactive Source

As an alternative to exciting the radioluminescent nanoparticles with an x-ray beam generated by an x-ray tube, embodiments of the invention also include excitation of the radioluminescent nanoparticles using a radioactive material. This has several advantages over using an electrical x-ray source. Radioactive materials are more compact than typical x-ray tubes, and therefore can be easily used in endoscopic applications. Radioactive materials can be selected to emit gamma radiation or beta radiation. In some applications, only a small volume of tissue should be irradiated, hence, the short range of electrons in tissue gives beta radiation an advantage over gamma radiation and x-rays. Unlike x-ray tubes, radioactive materials do not require cooling and can be operated continuously.

Figure 3:
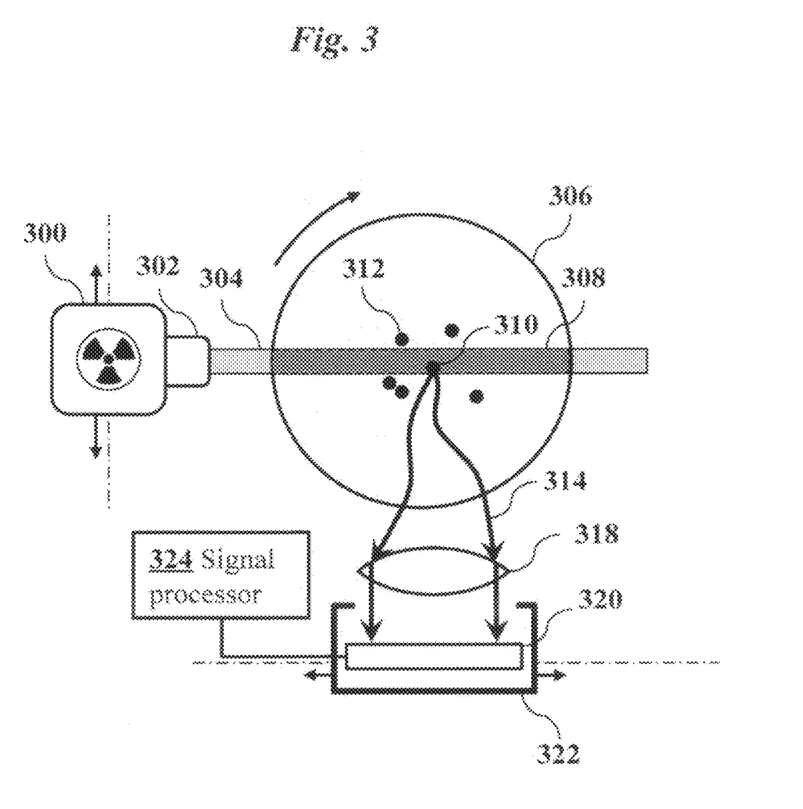
FIG. 3 is a schematic diagram of a system for molecular imaging using a radioactive source, according to an embodiment of the invention.

Accordingly, in some embodiments, the selected region of the biological tissue is irradiated with ionizing radiation from a radioactive source, as shown in FIG. 3. A source 300 includes one or more types of radioactive material encased in a shielded container (e.g., lead) with a collimating opening 302. The radioactive material emits ionizing radiation, which may include alpha, beta, gamma, and/or x-ray radiation. The collimator 302 forms the radiation in a beam 304 directed toward the biological tissue 306. The intersection of the beam 304 with the tissue 306 determines a selected region 308. Radioluminescent nanoparticle probes in the selected region are thus irradiated and emit radioluminescent optical wavelength light, while nanoparticle probes outside the selected region are not irradiated and so do not emit radioluminescent light. For example, probe 310 in the selected region 308 is irradiated and emits optical wavelength light 314, while probe 312 outside the selected region 308 is not irradiated and emits no light.

The source 300 is preferably positioned near the biological tissue. The collimator 302 may be designed to create a narrow beam 304, as shown in FIG. 3. In alternate embodiments, the collimator 302 may be designed to create a broad cone beam which may irradiate and select a significantly larger region of the tissue. Optical wavelength light 314 from irradiated probes in the selected region 308 is coupled by a lens 318 and detected by a photodetector 320, e.g., a near-infrared (NIR) detector. The lens 318 may be designed to selectively focus on the detector 320 optical light from a selected portion of the irradiated region 308. In some embodiments, especially those where the source 300 produces a wide beam of ionizing radiation, a shielded casing 322 (e.g., made of lead) surrounds detector 320 to reduce effects of the ionizing radiation 304 on the operation of the detector.

In some embodiments, the source 300 and/or detection system, which includes the lens 318 and detector 320, may be computer-controlled to independently translate along orthogonal axes to different positions. Alternatively, or in addition, the tissue 306 may be rotated to different rotational orientations relative to the source and detector system. During such a scanning procedure, signals from the detector 320 are recorded at each of a sequence of translational and/or rotational positions to produce a set of signals which may be combined by a signal processor 324 to produce a tomographic reconstruction of the spatial distribution of the radioluminescent nanoparticle probes in the biological tissue.

In some embodiments, the radioactive source 300 is not present, or not used. Instead, either 1) the molecular probes themselves contain a radioactive material bound to them (preferably a short-range beta emitter), 2) another radiopharmaceutical compound is injected into a selected region of the biological tissue, or 3) radioactive seeds used for brachytherapy are used as sources of ionizing radiation. Thus, the ionizing radiation is emitted from a radioactive source within the tissue, thereby irradiating nearby radioluminescent nanoparticles, resulting in the emission of radioluminescent optical wavelength light. In these embodiments, the detector 322 detects the light and the signals resulting from the detection of the optical signals are then processed for determining the spatial distribution of the molecular probes and/or assessing a presence and concentration of the molecular probes in the biological tissue 306. For example, the signals may be processed to produce an image representative of the spatial distribution of the irradiated molecular probes in the biological tissue. Scanning using translation and/or rotation relative to the tissue may be used with tomographic reconstruction.

Endoscopic Detector

Figure 4A:
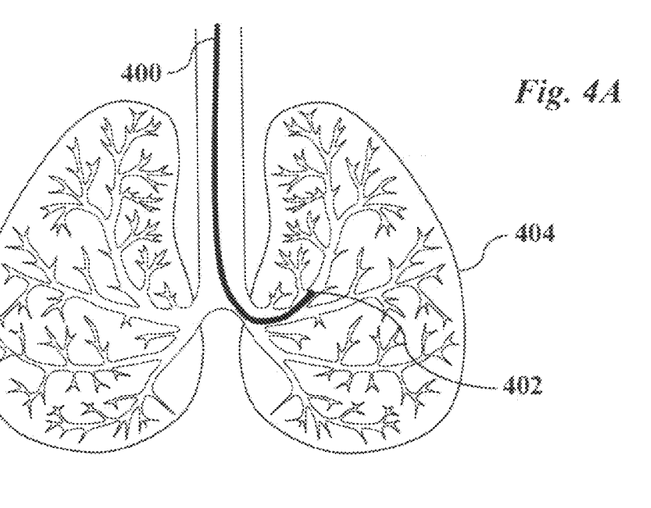
FIGS. 4A-B illustrate a system for molecular imaging using an endoscope, according to an embodiment of the invention.
Figure 4B:
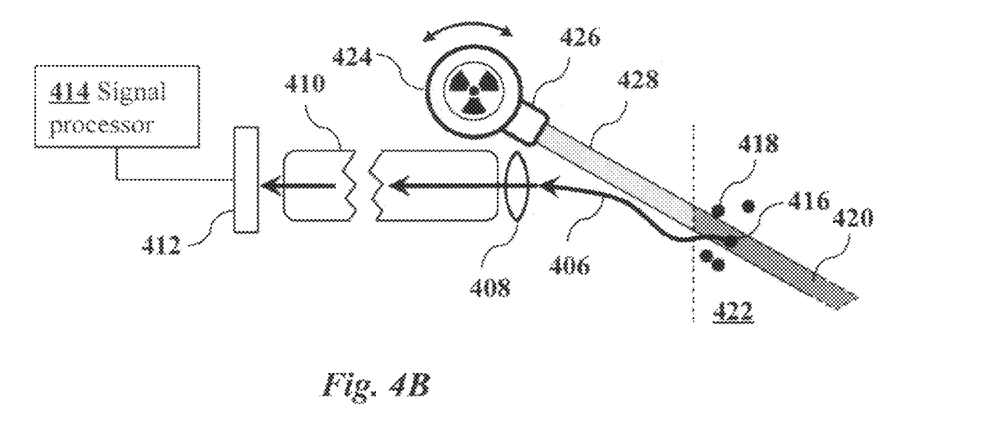

In another embodiment, an endoscopic device is used for molecular imaging, as shown in FIGS. 4A-B, where an endoscope 400 is shown for illustrative purposes inserted into a lung 404. In general, such an endoscope may be placed in any of various body cavities e.g., the gastrointestinal tract, the esophagus, the cardiovascular system, the pulmonary system, or the urinary tract. The endoscope 400 has a distal end 402 where light 406 is coupled through a lens 408 and waveguide 410, such as an optical fiber, fiber bundle, or liquid light guide, to a photodetector 412, e.g., NIR detector, at the proximal end of the endoscope. When the distal end 402 is positioned near radioluminescent probes 416 that have been irradiated by ionizing radiation, optical wavelength radioluminescent light 406 emitted form the probes 416 is detected by the detector 412. A signal processor 414 analyzes the detected signals to determine the presence and/or concentration of molecular probes near the distal end of the endoscope. In an alternate embodiment, detector 412 is positioned at the distal end 402 and the optical waveguide 410 is replaced by an electronic coupling between the detector 412 and signal processor 414.

In some embodiments, the distal end 402 of the endoscope 400 includes a radioactive source 424 that irradiates nearby molecular probes with ionizing radiation, in a manner similar to source 300 (FIG. 3). Such a source 424 may be shielded and have a collimator 426 to create a beam of ionizing radiation 428 in a selected direction. In some embodiments, the source may be rotated or otherwise positioned, either manually or by automatic computer-controlled scanning, to direct the beam 428 so that it selectively irradiates a region 420 of tissue 422. For example, probe 416 in region 420 is irradiated by beam 428, while probe 418 is not. In another embodiment, source 424 has a retractable shield, e.g., a cover of the collimator 426, which can be controlled to selectively prevent the ionizing radiation from exiting the source when unnecessary and allow the radiation beam 428 to exit the source when required for imaging. Such a shield could also be operated to provide differential optical information, e.g., by comparison of the background optical signal with the beam 428 off with the optical signal detected when the beam 428 is on.

In other embodiments, the source 424 is either not present or not used. Instead, the radioluminescent nanoparticle probes in tissue near the distal end of the endoscope are irradiated by ionizing radiation from a radiopharmaceutical material injected into the tissue, as described in relation to other embodiments above.

These endoscopic techniques provide advantages for endoscopic biopsies, which traditionally are guided by 3-dimensional diagnostic images acquired prior to the procedure and by 2-dimensional fluoroscopic or x-ray projection images during the procedure to verify endoscope position. However, these 2-dimensional images have poor diagnostic quality compared to the earlier 3-dimensional images. Thus, surgical biopsy has a limited ability to discriminate diseased from normal tissue. This leads to poor tissue sampling, which in turn results in improper staging of cancers, and increase in tissue injury due to multiple biopsies. In many cases, the uncertain diagnosis requires more extensive interthoracic surgical biopsy. This more invasive procedure imposes significant costs and increased healing time.

The endoscopic molecular imaging technique of the present invention allows the clinician to visualize biological targets such as lesions or lymph nodes during the procedure with optical fiber located in an endoscope. This enables structural imaging of the tissue with high resolution while simultaneously enabling molecular imaging. In this case, the physician can localize the molecular probes by looking for light emitters.

The fiber optic-based light coupling can be modified to collect a larger volume of light by cleaving the distal end of the fibers at an oblique angle to the direction of light propagation. This increases the sensitivity of the fibers to volumes normal to the direction of light propagation. This design can be used to reduce the manual angling of the tip of the endoscope, which risks damage to the tissue such as pneumothorax.

Needle biopsies are also plagued by poor sampling localization because of the lack accurate and specific imaging tools during the procedure. Current tools used in biopsy do not have sufficient diagnostic quality to image the full extent of a lesion with high accuracy. However, embodiments of the invention allow the clinician to visualize disease by simply inserting an optical fiber into the needle channel, in the same manner that the fiber is inserted in the endoscope described above. During x-ray guidance, the radioluminescent nanoparticles enable the clinician to better visualize the volumes with the greatest probability for disease. Thus, this technique alleviates the need for pre-biopsy wire localization, and allow for better sampling of the lesion.

Mammography

Figure 5:
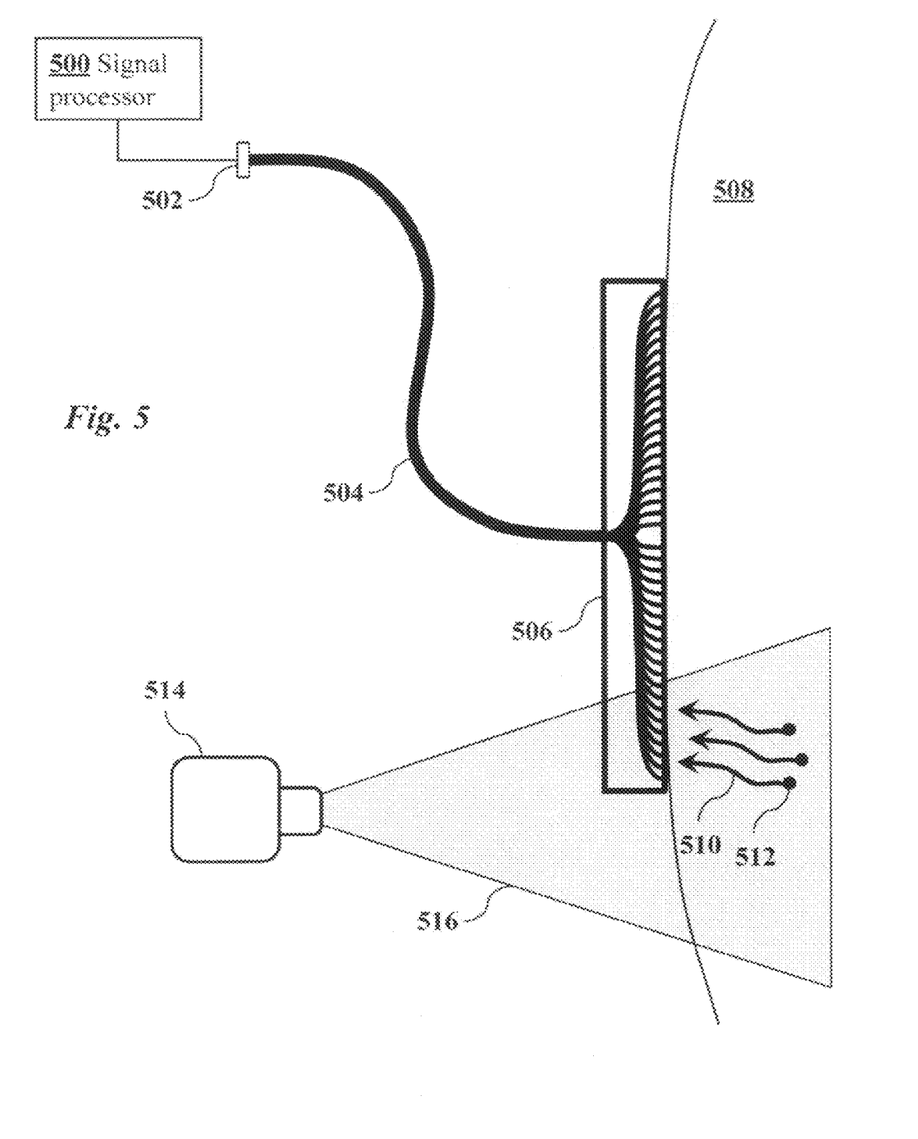
FIG. 5 is a schematic diagram of a system for molecular imaging using a mammography paddle, according to an embodiment of the invention.

Embodiments of the invention also have application to mammography, which still struggles with achieving contrast resolution sufficient to differentiate small structures from background tissue. Currently available mammography often results in poor discrimination among normal and pathologic processes, obscuring even very large lesions. However, embodiments of the invention can be used with a mammography unit to provide great effectiveness, as illustrated in FIG. 5. Optical fibers from a fiber bundle 504 terminating in the surface of a clear mammographic compression paddle 506 transmit light 510 from irradiated nanoparticles 512 to the distal end of a fiber bundle or lens-coupled imaging device 502, providing signals representative of radioluminescent nanoparticle concentration. A signal processor 500 analyzes the signals to produce data indicative of the presence or concentration of nanoparticles in the region of tissue irradiated by a beam 516 of ionizing radiation from source 514. Due to its low Z-number and thin dimensions, fiber bundle 504 will attenuate the x-ray very little. In another embodiment, the fibers are not spread out over the surface of the paddle 506, but localized and translated around the compression paddle during imaging, resulting in images on a photodetector 502 corresponding to the different translation positions. A calibration routine will un-distort the illumination from the proximal end to mimic the image on the distal end. Thus, this system will allow accurate co-registration with mammography. Suspicious lesions indicated with mammography can be inspected further with molecular imaging. Alternatively, the breast may be scanned to detect mammographically occult lesions. This system would enable current mammography to perform disease-specific molecular imaging, increasing the utility of currently used imaging hardware.

Capsule Endoscope

In other embodiments, the optical light may be detected by miniature photodetectors within a capsule endoscope. The radioluminescent nanoparticle probes in tissue near the distal end of the capsule endoscope are irradiated by ionizing radiation from a radiopharmaceutical material injected into the tissue, as described in relation to other embodiments above, or by a radioactive material in the capsule endoscope. Such a capsule endoscope could have a design and operation much like that of the distal end of the endoscope described above in relation to FIGS. 4A-B.

The invention claimed is:

1. A method for molecular imaging comprising:
irradiating a selected region of a biological tissue with ionizing radiation to induce radioluminescence emission of optical light from irradiated molecular probes located in the selected region, wherein the molecular probes preferentially bind to a predetermined biological target within the biological tissue, wherein the molecular probes comprise radioluminescent nanoparticles;
detecting the optical light from the irradiated molecular probes to produce signals;
processing the signals to determine a spatial distribution of the irradiated molecular probes in the biological tissue.

2. The method of claim 1 wherein the radioluminescent nanoparticles comprise inorganic phosphors, scintillators, or quantum dots.

3. The method of claim 1 wherein the radioluminescent nanoparticles comprise organic phosphors, scintillators, or quantum dots.

4. The method of claim 1 wherein the radioluminescent emission of optical light comprises emission at a predetermined near infrared (NIR) wavelength.

5. The method of claim 1 wherein the radioluminescent nanoparticles comprise at least two distinct types of material having distinct predetermined optical emission wavelengths.

6. The method of claim 1, further comprising injecting a radiopharmaceutical compound into the biological tissue, and wherein the ionizing radiation irradiating the selected region of the biological tissue originates from the injected radiopharmaceutical compound.

7. The method of claim 1 wherein irradiating a selected region of the biological tissue with ionizing radiation comprises scanning the biological tissue with a computer-controlled collimated x-ray beam to select a sequence of distinct selected regions.

8. The method of claim 1 wherein irradiating a selected region of the biological tissue with ionizing radiation comprises positioning an endoscope near the selected region, wherein the endoscope comprises a radioactive material producing the ionizing radiation.

9. The method of claim 8 wherein the endoscope comprises a retractable shield to selectively block the ionizing radiation, and collimators to selectively direct the ionizing radiation.

10. The method of claim 1 wherein the ionizing radiation comprises alpha particles, beta particles (electrons or positrons), electron beams, proton beams, gamma rays, ultraviolet light, or x-ray radiation.

11. The method of claim 1 wherein detecting the optical light from the irradiated molecular probes comprises coupling the optical light through an endoscope from a distal end to a photodetector at a proximal end.

12. The method of claim 1 wherein detecting the optical light from the irradiated molecular probes is performed by photodetectors within a capsule endoscope.

13. The method of claim 1 wherein detecting the optical light from the irradiated molecular probes is performed by an array of photodetectors screened from x-ray interference.

14. The method of claim 1 wherein processing the signals comprises producing an image representative of the spatial distribution of the irradiated molecular probes in the biological tissue.

15. The method of claim 1 wherein processing the signals comprises assessing a presence and concentration of the irradiated molecular probes in the biological tissue.

16. The method of claim 1 wherein processing the signals comprises tomographic reconstruction of the spatial distribution of the irradiated molecular probes in the biological tissue.

17. The method of claim 1 further comprising performing simultaneous x-ray imaging of the biological tissue to produce x-ray imaging data, and performing co-registration of the x-ray imaging data with the spatial distribution of the irradiated molecular probes.

* * * * *